(12) United States Patent
Shenai-Khatkhate et al.

(10) Patent No.: US 6,680,397 B2
(45) Date of Patent: Jan. 20, 2004

(54) ORGANOINDIUM COMPOUNDS

(75) Inventors: Deodatta Vinayak Shenai-Khatkhate, Danvers, MA (US); Ronald L. DiCarlo, Jr., Newfields, NH (US)

(73) Assignee: Shipley Company, L.L.C., Marlborough, MA (US)

( * ) Notice: Subject to any disclaimer, the term of this patent is extended or adjusted under 35 U.S.C. 154(b) by 0 days.

(21) Appl. No.: 10/346,585

(22) Filed: Jan. 17, 2003

(65) Prior Publication Data

US 2003/0181745 A1 Sep. 25, 2003

Related U.S. Application Data

(60) Provisional application No. 60/349,726, filed on Jan. 17, 2002, and provisional application No. 60/395,169, filed on Jul. 11, 2002.

(51) Int. Cl.$^7$ .............. C07F 5/00; C23C 16/00; H01L 21/44
(52) U.S. Cl. .............. 556/1; 427/252; 427/593; 438/680; 438/681
(58) Field of Search .............. 556/1; 427/252, 427/593; 438/681, 680

(56) References Cited

U.S. PATENT DOCUMENTS

| | | | | |
|---|---|---|---|---|
| 3,310,574 A | * | 3/1967 | Todt et al. | 556/1 |
| 4,720,560 A | | 1/1988 | Hui et al. | 556/1 |
| 4,847,399 A | | 7/1989 | Hallock et al. | 556/1 |
| 5,502,227 A | | 3/1996 | Kanjolia et al. | 556/1 |
| 5,863,836 A | | 1/1999 | Jones | 438/681 |

FOREIGN PATENT DOCUMENTS

WO    WO 00/37710    6/2000

* cited by examiner

*Primary Examiner*—Porfirio Nazario-Gonzalez
(74) *Attorney, Agent, or Firm*—S. Matthew Cairns

(57) ABSTRACT

Disclosed are trialkylindium compounds containing two bulky alkyl groups that are liquids or easily liquefiable solids and have sufficient vapor pressure for use in vapor deposition processes, as well as methods of depositing indium containing films using such compounds.

19 Claims, No Drawings

ORGANOINDIUM COMPOUNDS

This application claims the benefit of U.S. Provisional Application(s) No(s). 60/349,726 filed Jan. 17, 2002 and 60/395,169 filed Jul. 11, 2002.

BACKGROUND OF THE INVENTION

The present invention relates generally to the field of organometallic compounds. In particular, the present invention relates to the certain indium compounds suitable for use in indium vapor deposition processes.

Metal films may be deposited on surfaces, such as non-conductive surfaces, by a variety of means such as chemical vapor deposition ("CVD"), physical vapor deposition ("PVD"), and other epitaxial techniques such as liquid phase epitaxy ("LPE"), molecular beam epitaxy ("MBE"), and chemical beam epitaxy ("CBE"). Chemical vapor deposition processes, such as metalorganic chemical vapor deposition ("MOCVD"), deposit a metal layer by decomposing organometallic precursor compounds at elevated temperatures, i.e., above room temperature, either atmosphere pressure or at reduced pressures.

A wide variety of metals may be deposited using such CVD or MOCVD processes. See, for example, Stringfellow, *Organometallic Vapor Phase Epitaxy: Theory and Practice*, Academic Press, $2^{nd}$ Edition, 1999, for an overview of such processes. For example, indium is used in a variety of metal films produced by epitaxial growth, particularly in the manufacture of electronic devices such as integrated circuits and light emitting diodes ("LEDs"). Exemplary indium containing metal films include indium-phosphide ("InP"), indium-gallium-arsenide ("InGaAs"), indium-gallium-aluminum-phosphide ("InGaAlP"), indium-gallium-arsenic-phosphide ("InGaAsP"), indium-gallium-arsenide/gallium-arsenide/aluminum-gallium-arsenide ("InGaAs/GaAs/AlGaAs"), indium-arsenide ("InAs"), indium-antimonide ("InSb") and indium-arsenic-bismuthide ("InAsBi").

Metal layers and alloy layers are typically formed in CVD or MOCVD processes by the decomposition of one or more precursor compounds. A wide variety of precursor compounds may be used. In conventional CVD processes, suitable precursor compounds must have a sufficient vapor pressure to allow them to be transported to the deposition chamber. From ease of handling and transportation to the deposition chamber, liquid precursor compounds are preferred.

A number of indium compounds are known as CVD and/or MOCVD precursors. Solid trimethylindium is the conventional precursor of choice for use in the manufacture of indium-containing semiconductors. However, this compound imposes several problems during the growth of indium-containing alloys because of inconsistency in the compound's evaporation rate when a conventional bubbler-type container is used in the delivery system. Such inconsistency in the vapor phase concentration of trimethylindium has been attributed to a) reduction in the surface area of the solid trimethylindium with the progress of growth, b) formation of voids or channels in the solid trimethylindium that offer only minimal contact with the carrier gas, c) sublimation of the trimethylindium to regions of the delivery system inaccessible to the carrier gas flow, and d) recrystallization of the trimethylindium leading to changes in its surface area that prohibit evaporation.

Various attempts have been tried to overcome these difficulties, but have had limited success. These have included reversing the direction of carrier gas flow, depositing the indium precursor on an inert porous solid support, suspending the precursor in a liquid medium, suspending the precursor in another alkylindium and using hybrid organoindium compounds instead of trimethylindium. For example, U.S. Pat. No. 4,720,560 (Hui et al.) discloses hybrid organometallic compounds having the formula MRx where x=2–4; the Rs are independently selected from hydrogen, lower alkyl, phenyl, alkyl substituted phenyl, cyclopentadienyl, or alkyl substituted cyclopentadienyl; M is an element of Groups 2B or 3A of the periodic table, bismuth, selenium, tellurium, beryllium and magnesium; wherein at least 2 of the Rs are different. The only indium compounds disclosed in this patent are dimethylethylindium and diethylmethylindium. These indium compounds have not achieved commercial success because they do not have a sufficiently high vapor pressure and because they do not exist as a single species. Both dimethylethylindium and diethylmethylindium exist as an equilibrium with trimethylindium and triethylindium, such equilibrium being temperature dependent. Such an equilibrium mixture is disadvantageous because during the vapor deposition process, the more volatile trimethylindium will be consumed first, and the less volatile triethylindium second. However, because of the differences (mismatch) in vapor pressure between these compounds, a lesser volume of triethylindium may be transported to the deposition chamber, thus adversely affecting the quality of the indium film deposited.

Though trimethylindium is a solid, it is the only indium compound to achieve commercial success because of its higher vapor pressure. Methods of providing trimethylindium in liquid form have been sought. For example, a solution of trimethylindium in a solvent has been sold commercially. This may be problematic in that impurities in the solvent or the solvent itself may contaminate the deposited indium film. Trimethylindium has also been dissolved in tri($C_3$–$C_5$)alkylindiums. See, e.g., U.S. Pat. No. 5,502,227, which discloses a solution of trimethylindium dissolved in a high boiling tri($C_3$–$C_5$)alkylindium, such as tripropylindium, tri-n-butylindium or tri-iso-butylindium. Such higher boiling trialkylindiums are reported to be more advantageous solvents than organic solvents as any impurities would have been removed during purification of the trialkylindium or else they would react with the trialkylindium before the addition of the trimethylindium. However, such approach requires a higher temperature during deposition, such as 17° to 40° C., in order to keep the equilibrium shifted such that trimethylindium is the predominate compound.

Another problem with trimethylindium is that films (pure indium or indium alloys) grown from trimethylindium suffer from high carbon incorporation. Triethylindium is used in applications where indium films having low carbon content are desired. Indium films grown from triethylindium have a lower carbon content than films grown from trimethylindium. One problem with triethylindium is that it has a lower vapor pressure than trimethylindium and consequently has a lower concentration in the vapor phase. Triethylindium is not suitable for forming indium alloys, such as indium phosphide.

There is thus a need for liquid indium compounds having sufficient vapor pressure to be suitable for use as a CVD and/or MOCVD indium precursor compound.

SUMMARY OF THE INVENTION

It has been surprisingly found that certain trialkylindium compounds are liquids at room temperature, are discrete species and have sufficient vapor pressure suitable for use as CVD and/or MOCVD indium precursor compounds.

In one aspect, the present invention provides an indium compound having the formula $Bg^1Bg^2InR$, wherein $Bg^1$ and $Bg^2$ are bulky alkyl groups each having at least three carbons, and R is a $(C_1-C_4)$alkyl, where R and $Bg^1$ are different. Such indium compound is particularly suitable for use as a CVD and/or MOCVD precursor compound.

In a second aspect, the present invention provides a method for depositing a film including indium on a substrate including the steps of: a) conveying a trialkylindium compound of the formula $Bg^1Bg^2InR$, wherein $Bg^1$ and $Bg^2$ are bulky alkyl groups each having at least three carbons, and R is a $(C_1-C_4)$alkyl, where R and $Bg^1$ are different, in the gaseous phase to a deposition chamber containing the substrate; b) decomposing the trialkylindium compound in the deposition chamber; and c) depositing a film including indium on the substrate.

In a third aspect, the present invention provides a method for manufacturing an electronic device including the step of depositing a film including indium on an electronic device substrate including the steps of: a) conveying a trialkylindium compound of the formula $Bg^1Bg^2InR$, wherein $Bg^1$ and $Bg^2$ are bulky alkyl groups each having at least three carbons, and R is a $(C_1-C_4)$alkyl, where R and $Bg^1$ are different, in the gaseous phase to a deposition chamber containing the substrate; b) decomposing the trialkylindium compound in the deposition chamber; and c) depositing a film including indium on the substrate.

In a fourth aspect, the present invention provides a liquid indium compound suitable for use as a vapor deposition precursor compound, wherein the liquid indium compound is substantially a discrete species and liquid at room temperature.

DETAILED DESCRIPTION OF THE INVENTION

As used throughout this specification, the following abbreviations shall have the following meanings, unless the context clearly indicates otherwise: °C.=degrees centigrade; FTNMR=Fourier transform nuclear magnetic resonance; g=gram; L=liter; M=molar; ca.=approximately; mm=millimeters; Bg=bulky alkyl group; mol=moles; and mL=milliliter.

"Halo" refers to fluoro, chloro, bromo and iodo. Likewise, "halogenated" refers to fluorinated, chlorinated, brominated and iodinated. "Alkyl" includes linear, branched and cyclic alkyl. Unless otherwise noted, all amounts are percent by weight and all ratios are by weight. All numerical ranges are inclusive and combinable in any order, except where it is obvious that such numerical ranges are constrained to add up to 100%.

The present invention provides an indium compound suitable for use as a vapor deposition precursor compound, such as for CVD and/or MOCVD, and having the formula $Bg^1Bg^2InR$, wherein $Bg^1$ and $Bg^2$ are independently bulky alkyl groups each having at least three carbons, and R is a $(C_1-C_4)$alkyl, where R and $Bg^1$ are different. By "bulky alkyl group" is meant any group having sufficient steric hindrance to provide the indium compound in monomeric form, i.e. to prevent dimer, trimer, tetramer and higher order complex formation. Such bulky alkyl groups have at least three carbons, there being no particular upper limit to the number of carbons in such group. It is preferred that the bulky alkyl groups each have from three to six carbon atoms, more preferably three to five carbon atoms, still more preferably from three to four carbon atoms, and most preferably three carbon atoms. Such groups are preferably not linear, and are preferably cyclic or branched.

The bulky groups preferably are those capable of undergoing β-hydride elimination. It is preferred that at least one bulky group is capable of undergoing β-hydride elimination. Thus, preferred bulky groups contain a hydrogen bonded to the carbon in the beta position to the indium. Suitable bulky alkyl groups include, but are not limited to, tert-butyl, iso-propyl, iso-butyl, sec-butyl, cyclopentyl, methylcyclopentyl, cyclohexyl, methylcyclohexyl, and cyclopropyl, more preferably tert-butyl, iso-propyl, sec-butyl, and preferably tert-butyl and iso-propyl. Most preferred is iso-propyl. It is further preferred that at least one bulky alkyl group is iso-propyl. In an alternate embodiment, it is preferred that $Bg^1$ and $Bg^2$ are the same. When one bulky alkyl group has five or more carbons, it is preferred that the second bulky alkyl group has three to four carbon atoms. Any $(C_1-C_4)$alkyl group is suitable for R provided it is different from the group represented by $Bg^1$. It is preferred that the alkyl group of R is linear. Accordingly, it is preferred that R is methyl, ethyl, n-propyl or n-butyl, and more preferably methyl or ethyl.

The present indium compounds are heteroleptic, i.e. they are unsymmetrical. By "unsymmetrical" it is meant that the three groups bonded to the indium are not all the same. Two of the groups may be the same or all three of the groups may be different.

Particularly suitable indium precursor compounds are di-iso-propylmethylindium, di-iso-propylethylindium, di-iso-propyl-n-propylindium, iso-propyl-tert-butylmethylindium, iso-propyl-tert-butylethylindium, di-tert-butylmethylindium, di-tert-butylethylindium, iso-butyl-iso-propylmethylindium, iso-butyl-iso-propylethylindium, di-iso-butylmethylindium, di-iso-butylethylindium, and dicyclopentylmethylindium. Preferred indium compounds include di-iso-propylmethylindium, di-iso-propylethylindium, and iso-propyl-tert-butylmethylindium, and more preferably di-iso-propylmethylindium.

Such trialkylindium compounds may be prepared by a variety of methods known in the art. For example, the present compounds can be prepared by alkyl exchange reactions, such as between trimethylindium and tri-bulky group-indium compounds, or by reacting an indium halide with an alkyl lithium or Grignard reagent. Preferably, indium halides are reacted with an alkyl lithium reagent. Such a reaction is illustrated below where R and $Bg^1$ are as defined above.

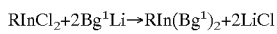

$$RInCl_2 + 2Bg^1Li \rightarrow RIn(Bg^1)_2 + 2LiCl$$

These reactions are typically carried out in a solvent. The reaction mixture may optionally be heated or cooled depending on the presence of an exotherm.

Any suitable organic solvent may be used. Preferably, the solvent is not an ether. While not intending to be bound by theory, the inventors believe that ether solvents tend to cause disproportionation of the present liquid indium compounds into symmetrical alkyl indium compounds. Particularly suitable organic solvents include, but are not limited to, hydrocarbons and aromatic hydrocarbons. Preferred organic solvents include benzene; alkyl benzenes such as toluene, xylene, and $(C_4-C_{20})$alkyl benzenes such as $(C_{10}-C_{12})$alkyl benzenes and $(C_{10}-C_{20})$alkyl biphenyls; aliphatic hydrocarbons such as pentane, hexane, heptane, octane, decane, dodecane, squalane, cyclopentane, and cyclohexane; and mixtures thereof. More preferably, the organic solvent is benzene, toluene, xylene, ($C_4$–$C_{20}$)alkyl benzenes, hexane, heptane, cyclopentane or cyclohexane. It will be appreciated that mixtures of organic solvents may be advantageously used in the present invention.

Preferably, such organic solvents are deoxygenated prior to use. The solvents may be deoxygenated by a variety of means, such as purging with an inert gas, degassing the solvent in vacuo, or a combination thereof. Suitable inert gases include argon, nitrogen and helium, and preferably argon or nitrogen.

The present liquid indium compounds may be purified by a variety of means, such as by distillation. Such purification methods are well known to those skilled in the art. Suitable purification methods are those disclosed in U.S. Pat. No. 4,847,399 (Hallock et al.).

The trialkylindium compounds of the present invention are typically liquids at or near room temperature or relatively easily liquefiable solids, and preferably liquids. It is preferred that the present compounds are liquid at or near room temperature (i.e. 22–28° C.) without the need for a solvent. Such compounds have sufficiently high vapor pressures to be suitable as precursor compounds for use in vapor deposition processes, such as CVD, MOCVD and other epitaxial techniques.

The present trialkylindium compounds are substantially separate or discrete species. By "substantially separate or discrete species" it is meant that they are monomeric and $\leq 1\%$, preferably $\leq 0.5\%$ and more preferably $\leq 0.1\%$ exist as dimers, trimers, tetramers or other higher order complexes. Preferably, the present compounds do not exist as dimers, trimers, tetramers or higher order complexes. The present trialkylindium compounds do not substantially (i.e. <1%, preferably <0.5% and more preferably <0.1%) dissociate during storage and are preferably free of dissociation. Thus, the present invention provides liquid indium compounds suitable for use as chemical vapor deposition and/or metalorganic chemical vapor deposition precursor compounds, wherein the liquid indium compounds are substantially discrete species. The compounds of the present invention are substantially free of organic solvents. The present trialkylindium compounds are preferably substantially free of detectable levels of silicon, tin, germanium and zinc, i.e. they contain <1 ppm of such impurities. Preferably, the present compounds are free of detectable levels of such impurities.

Indium films are typically deposited by first placing the desired indium precursor compound, or source compound, in a bubbler, or other delivery device suitable for delivering the present compounds in the gaseous phase having an outlet connected to a deposition chamber. A wide variety of bubblers may be used and are well-known to those skilled in the art. The particular bubbler will depend in part on the particular deposition apparatus used. The source compounds of the present invention are maintained in the bubbler as liquids or easily liquefiable solids. Solid source compounds are typically liquefied or sublimed prior to transportation to the deposition chamber. The source compound is typically transported to the deposition chamber by passing a carrier gas through the bubbler. Suitable carrier gasses include nitrogen, hydrogen, and mixtures thereof. In general, the carrier gas is introduced below the surface of the source compound, and bubbles up through the source compound to the headspace above it, entraining or carrying vapor of the source compound in the carrier gas. The entrained or carried vapor then passes into the deposition chamber.

The deposition chamber is typically a heated vessel within which is disposed at least one, and possibly many, substrates. The deposition chamber has an outlet, which is typically connected to a vacuum pump in order to draw by-products out of the chamber and to provide a reduced pressure where that is appropriate. MOCVD can be conducted at atmospheric or reduced pressure. The deposition chamber is maintained at a temperature sufficiently high to induce decomposition of the source compound. The typical deposition chamber temperature is from about 300° to about 1000° C., the exact temperature selected being optimized to provide efficient deposition. Such optimization is well within the ability of one skilled in the art. Optionally, the temperature in the deposition chamber as a whole can be reduced if the substrate is maintained at an elevated temperature, or if other energy such as radio frequency ("RF") energy is generated by an RF source.

Suitable substrates for deposition may be any upon which a film including indium is desired, such as, but not limited to silicon such as silicon wafers used in integrated circuit manufacture, gallium arsenide, indium phosphide, and the like. Such substrates are particularly useful in the manufacture of integration circuits.

Deposition is continued for as long as desired to produce a film having the desired properties. Typically, the film thickness will be from several hundred to several thousand angstroms or more when deposition is stopped.

The present trialkylindium compounds are useful in depositing any film containing indium, either as pure indium or as alloys thereof. Suitable films include, but are not limited to, indium, indium-phosphide ("InP"), indium-gallium-arsenide ("InGaAs"), indium-gallium-aluminum-phosphide ("InGaAlP"), indium-gallium-arsenic-phosphide ("InGaAsP"), indium-gallium-arsenide/gallium-arsenide/ aluminum-gallium-arsenide ("InGaAs/GaAs/AlGaAs"), indium-arsenide ("InAs"), indium-antimonide ("InSb") and indium-arsenic-bismuthide ("InAsBi").

Thus, the present invention provides a method for depositing a film including indium on a substrate including the steps of: a) conveying a trialkylindium compound of the formula $Bg^1Bg^2InR$, wherein $Bg^1$ and $Bg^2$ are bulky alkyl groups each having at least three carbons, and R is a ($C_1$–$C_4$)alkyl, where R and $Bg^1$ are different, in the gaseous phase to a deposition chamber containing the substrate; b) decomposing the trialkylindium compound in the deposition chamber; and c) depositing a film including indium on the substrate.

Also provided by the present invention is a method for manufacturing an electronic device including the step of depositing a film including indium on an electronic device substrate including the steps of: a) conveying a trialkylindium compound of the formula $Bg^1Bg^2InR$, wherein $Bg^1$ and $Bg^2$ are bulky alkyl groups each having at least three carbons, and R is a ($C_1$–$C_4$)alkyl, where R and $Bg^1$ are different, in the gaseous phase to a deposition chamber containing the substrate; b) decomposing the trialkylindium compound in the deposition chamber; and c) depositing a film including indium on the substrate.

Suitable electronic devices include, but are not limited to, integrated circuits and light emitting diodes ("LEDs").

The following examples are presented to illustrate further various aspects of the present invention, but are not intended to limit the scope of the invention in any aspect.

EXAMPLE 1

Di-iso-propylmethylindium was prepared as follows. Trimethylindium (1.6 g, 0.01 mol) and indium (III) chloride (4.4 g, 0.02 mol) were dispersed in ca. 50 mL of a mixture of linear alkyl benzenes (di/tri-isopropylbiphenyls) (Sursol™ 300, available from Koch Specialty Chemical Co.) in a reaction vessel. The reaction mixture was then heated to 100° C. After cooling, 100 mL of 0.7M iso-propyl lithium in pentane was added dropwise to the reaction mixture. Following addition of the iso-propyl lithium, the reaction mixture was heated under vacuum to distill all volatiles into a receiver cooled at −78° C. The contents of the receiver were then subjected to vacuum distillation to remove solvent. Approximately 3 mL of a heavy, oily, yellow liquid product was obtained. The product was analyzed by FTNMR spectroscopy and found to be di-iso-propylmethylindium.

EXAMPLE 2

The preparation of di-iso-propylmethylindium was attempted as follows. Indium (III) chloride (44 g) and 100 mL of a mixture of linear alkyl benzenes (di/tri-isopropylbiphenyls) (Sursol™ 300) was added to a reaction flask to which was added dropwise 400 mL of 2 M iso-propylmagnesium chloride in ether. Following addition, ether was removed by atmospheric distillation and tri-iso-propylindium was separated by vacuum distillation at 110° C. The tri-iso-propylindium was then further purified by vacuum distillation to remove trace ether.

To a flask where added stoichiometric amounts of trimethylindium (1 g) and tri-iso-propylindium (3 g). The initially clear liquid turned grey, indicating decomposition to indium metal. Analysis of the reaction mixture by NMR spectroscopy did not show the formation of di-iso-propylmethylindium.

EXAMPLE 3

The preparation of iso-propyldimethylindium was attempted as follows. Trimethylindium (10.5 g) and indium (III) chloride (7.2 g) were heated to 80° C. in squalane to form dimethylindium chloride. To this was added 45 mL of iso-propylmagnesium chloride in ether. All volatile components were removed by vacuum distillation. The crude product was then subjected to full vacuum to remove residual ether. Analysis of the product by FTNMR spectroscopy showed it to be trimethylindium etherate. No iso-propyldimethylindium was observed.

It is believed that the presence of ether caused the disproportionation of the heteroleptic trialkylindium compounds.

EXAMPLE 4

The preparation of di-tert-butylmethylindium was attempted as follows. Trimethylindium (10 g) and indium (III) chloride (27.5 g) were reacted in a flask containing 250 mL of a mixture of linear ($C_{10}$–$C_{12}$) alkyl benzenes (540 L alkylate™) as the hydrocarbon solvent. The reaction mixture was heated to 81° C. to facilitate the formulation of methylindium dichloride. To this reaction mixture was added dropwise 220 mL of 0.7 M tert-butyl lithium in pentane. Following addition, the pentane was removed from the reaction mixture by distillation at atmospheric pressure and the reaction mixture was then vacuum distilled, the reaction mass was heated to 100° C. under full vacuum. The receiver was found to contain white crystals and clear liquid pentane. Further purification to remove pentane yielded a while crystalline product. Analysis of the product by NMR spectroscopy indicated it to be trimethylindium and not di-tert-butylmethylindium as expected.

What is claimed is:

1. An indium compound having the formula $Bg^1Bg^2InR$, wherein $Bg^1$ and $Bg^2$ are each bulky alkyl groups each having at least three carbons, and R is a ($C_1$–$C_4$)alkyl, where R and $Bg^1$ are different.

2. The indium compound of claim 1 wherein each bulky alkyl group has from three to six carbon atoms.

3. The indium compound of claim 2 wherein each bulky alkyl group has from three to five carbon atoms.

4. The indium compound of claim 1 wherein the bulky alkyl groups are branched or cyclic alkyls.

5. The indium compound of claim 1 wherein $Bg^1$ and $Bg^2$ are independently chosen from tert-butyl, iso-propyl, iso-butyl, sec-butyl, cyclopentyl, methylcyclopentyl, cyclohexyl, methylcyclohexyl, and cyclopropyl.

6. The indium compound of claim 5 wherein $Bg^1$ and $Bg^2$ are independently chosen from tert-butyl, iso-propyl, and sec-butyl.

7. The indium compound of claim 1 wherein $Bg^1$ and $Bg^2$ are independently chosen from tert-butyl or iso-propyl, and R is methyl or ethyl.

8. The indium compound of claim 1 wherein the compound is di-iso-propylmethylindium.

9. The indium compound of claim 1 wherein the compound is di-iso-propylethylindium.

10. A liquid heteroleptic indium compound suitable for use as chemical vapor deposition and/or metalorganic chemical vapor deposition precursor compounds, wherein the liquid indium compound is substantially a discrete species.

11. A method for depositing a film comprising indium on a substrate comprising the steps of: a) conveying a trialkylindium compound of the formula $Bg^1Bg^2InR$, wherein $Bg^1$ and $Bg^2$ are each bulky alkyl groups each having at least three carbons, and R is a ($C_1$–$C_4$)alkyl, where R and $Bg^1$ are different in the gaseous phase to a deposition chamber containing the substrate; b) decomposing the trialkylindium compound in the deposition chamber; and c) depositing a film comprising indium on the substrate.

12. The method of claim 11 wherein the film is selected from indium-phosphide, indium-gallium-arsenide, indium-gallium-aluminum-phosphide, indium-gallium-arsenic-phosphide, indium-gallium-arsenide/gallium-arsenide/aluminum-galluim-arsenide, indium-arsenide, indium-antimonide and indium-arsenic-bismuthide.

13. The method of claim 11 wherein each bulky alkyl group has from three to six carbon atoms.

14. The method of claim 13 wherein each bulky alkyl group has from three to five carbon atoms.

15. The method of claim 11 wherein the bulky alkyl groups are branched or cyclic alkyls.

16. The method of claim 11 wherein $Bg^1$ and $Bg^2$ are independently chosen from tert-butyl, iso-propyl, iso-butyl, sec-butyl, cyclopentyl, methylcyclopentyl, cyclohexyl, methylcyclohexyl, and cyclopropyl.

17. The method of claim 16 wherein $Bg^1$ and $Bg^2$ are independently chosen from tert-butyl, iso-propyl, and sec-butyl.

18. The method of claim 11 wherein $Bg^1$ and $Bg^2$ are independently chosen from tert-butyl and iso-propyl, and R is methyl or ethyl.

19. A method for manufacturing an electronic device comprising the step of depositing a film comprising indium on an electronic device substrate comprising the steps of: a) conveying a trialkylindium compound of the formula $Bg^1Bg^2InR$, wherein $Bg^1$ and $Bg^2$ are each bulky alkyl groups each having at least three carbons, and R is a ($C_1$–$C_4$)alkyl, where R and $Bg^1$ are different, in the gaseous phase to a deposition chamber containing the substrate; b) decomposing the trialkylindium compound in the deposition chamber; and c) depositing a film comprising indium on the substrate.

* * * * *